(12) United States Patent
Gough et al.

(10) Patent No.: US 7,691,087 B2
(45) Date of Patent: Apr. 6, 2010

(54) INJECTION DEVICE

(75) Inventors: Edward J. Gough, Sacramento, CA (US); Alan Stein, Bellingham, WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 440 days.

(21) Appl. No.: 10/723,476

(22) Filed: Nov. 25, 2003

(65) Prior Publication Data
US 2004/0158136 A1    Aug. 12, 2004

(51) Int. Cl.
*A61F 2/00* (2006.01)
(52) U.S. Cl. .................. 604/165.01; 600/29
(58) Field of Classification Search ............ 604/165.01, 604/164.01; 600/29; 128/DIG. 25
See application file for complete search history.

(56) References Cited

U.S. PATENT DOCUMENTS

| | | | |
|---|---|---|---|
| 4,609,370 A * | 9/1986 | Morrison ............ | 604/165.01 |
| 4,803,075 A | 2/1989 | Wallace et al. | |
| 5,007,940 A | 4/1991 | Berg | |
| 5,116,387 A | 5/1992 | Berg | |
| 5,158,573 A | 10/1992 | Berg | |
| 5,385,561 A | 1/1995 | Cerny | |
| 5,451,406 A | 9/1995 | Lawin et al. | |
| 5,580,568 A | 12/1996 | Greff et al. | |
| 5,637,075 A * | 6/1997 | Kikawada ............ | 600/153 |
| 5,667,767 A | 9/1997 | Greff et al. | |
| 5,695,480 A | 12/1997 | Evans et al. | |
| 5,855,615 A | 1/1999 | Bley et al. | |
| 6,146,373 A | 11/2000 | Cragg et al. | |
| 6,228,059 B1 * | 5/2001 | Astarita ............ | 604/164.07 |
| 6,231,613 B1 | 5/2001 | Greff et al. | |
| 6,234,955 B1 | 5/2001 | Silverman et al. | |
| 6,238,335 B1 | 5/2001 | Silverman et al. | |
| 6,248,058 B1 * | 6/2001 | Silverman et al. ............ | 600/29 |
| 6,251,063 B1 * | 6/2001 | Silverman et al. ............ | 600/29 |
| 6,251,064 B1 * | 6/2001 | Silverman et al. ............ | 600/29 |

(Continued)

FOREIGN PATENT DOCUMENTS

JP    59-37534 UA    3/1984

(Continued)

OTHER PUBLICATIONS

Walker et al., "Injectable Bioglass as a Potential Substitute for Injectable Polytetrafluorethylene Particles", *J. Urol.*, 1992, 148: 645-647.

*Primary Examiner*—Nicholas D Lucchesi
*Assistant Examiner*—Laura A Bouchelle
(74) *Attorney, Agent, or Firm*—Dorsey & Whitney LLP

(57) ABSTRACT

An injection device for use with tissue of a mammalian body comprising a first tubular member and a second tubular member slidably disposed in the first tubular member. The first and second tubular members have respective proximal and distal extremities. The distal extremity of the second tubular member is provided with a needle that is extendable from the distal extremity of the first tubular member. The proximal extremity of the second tubular member is lockable relative to the proximal extremity of the first tubular member. The second tubular member has a column strength when locked within the first tubular member for limiting retraction of the second tubular member relative to the first tubular member during puncture of the tissue by the needle.

15 Claims, 7 Drawing Sheets

U.S. PATENT DOCUMENTS

| | | | |
|---|---|---|---|
| 6,296,607 | B1 | 10/2001 | Milbocker et al. |
| 6,335,028 | B1 | 1/2002 | Vogel et al. |
| 6,358,197 | B1 | 3/2002 | Silverman et al. |
| 6,478,775 | B1 | 11/2002 | Galt et al. |
| 6,503,244 | B2 | 1/2003 | Hayman |
| 6,524,327 | B1 | 2/2003 | Spacek |
| 6,540,789 | B1 | 4/2003 | Silverman et al. |
| 6,565,551 | B1 | 5/2003 | Jones et al. |
| 6,595,901 | B2 | 7/2003 | Reinbold et al. |
| 6,595,910 | B2 | 7/2003 | Silverman et al. |
| 6,699,222 | B1 | 3/2004 | Jones et al. |
| 6,711,426 | B2 | 3/2004 | Benaron et al. |
| 2001/0051822 | A1* | 12/2001 | Stack et al. ................ 623/1.11 |
| 2002/0049363 | A1 | 4/2002 | Milbocker |
| 2003/0135238 | A1 | 7/2003 | Milbocker |
| 2004/0010192 | A1 | 1/2004 | Benaron |

FOREIGN PATENT DOCUMENTS

| | | |
|---|---|---|
| JP | 9-276275 A | 10/1997 |
| WO | WO 97/45131 A1 | 12/1997 |
| WO | 00/33908 | 6/2000 |
| WO | WO 00/33908 A1 | 6/2000 |
| WO | WO 01/35841 A1 | 5/2001 |
| WO | WO 02/36179 A3 | 5/2002 |

* cited by examiner

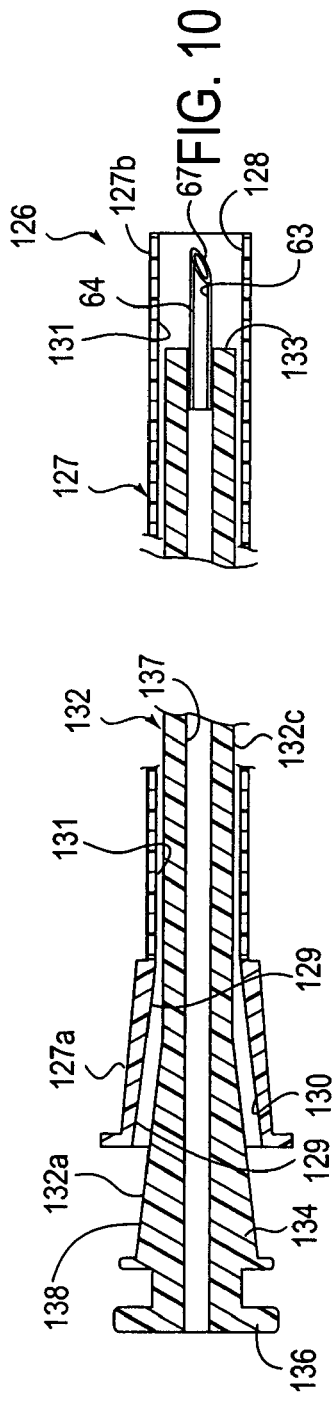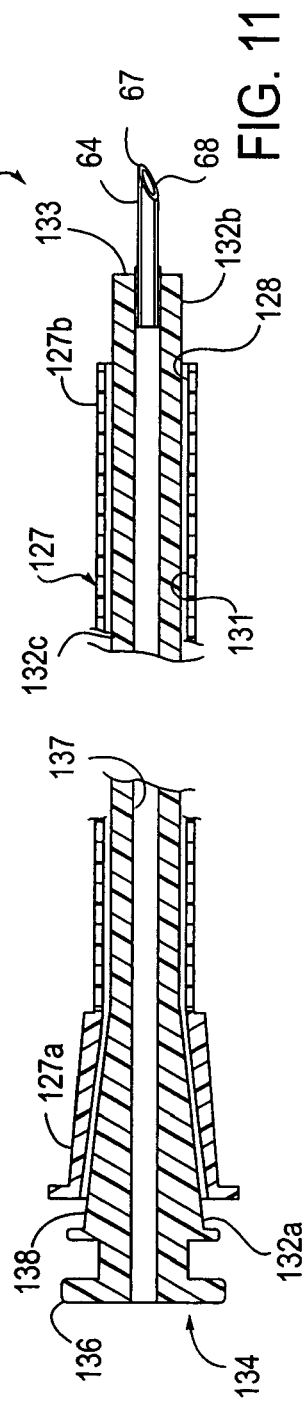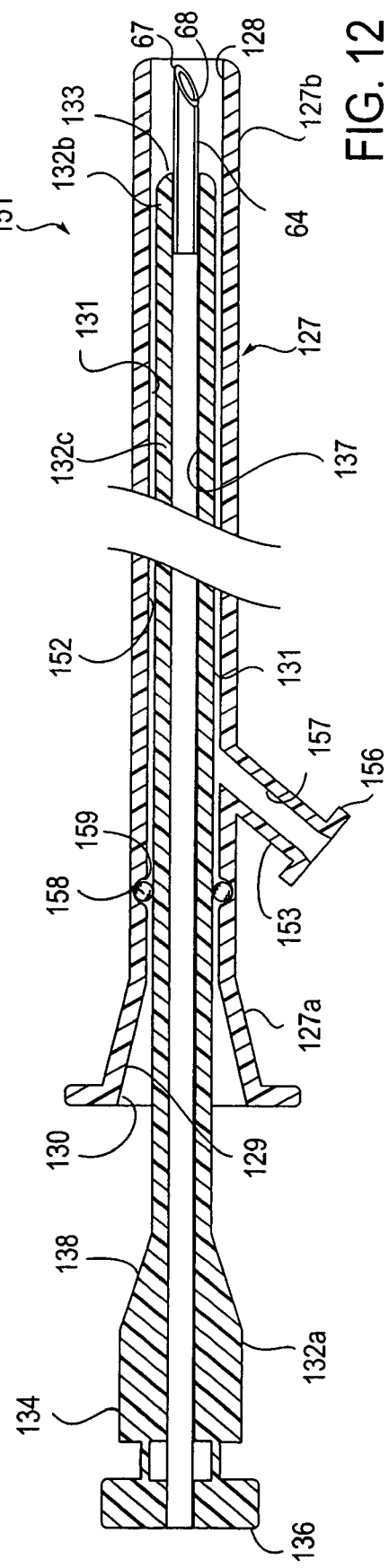

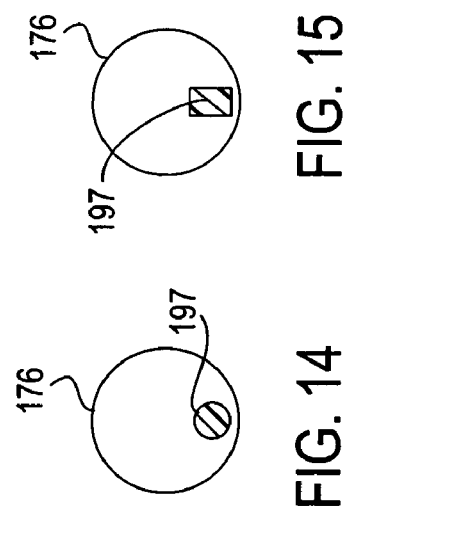
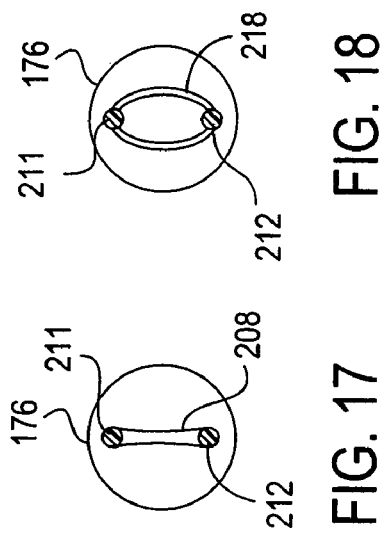
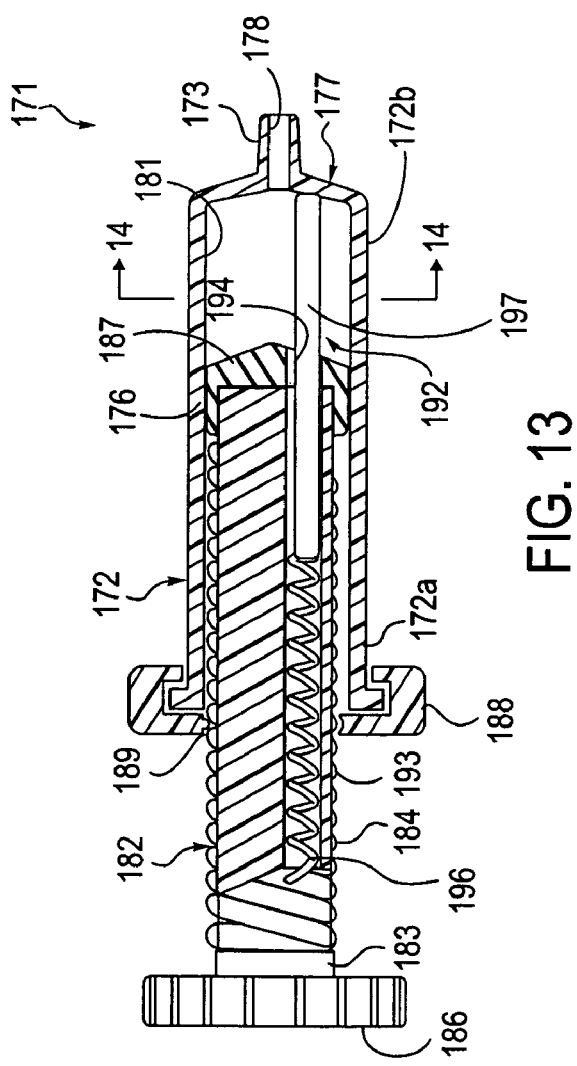
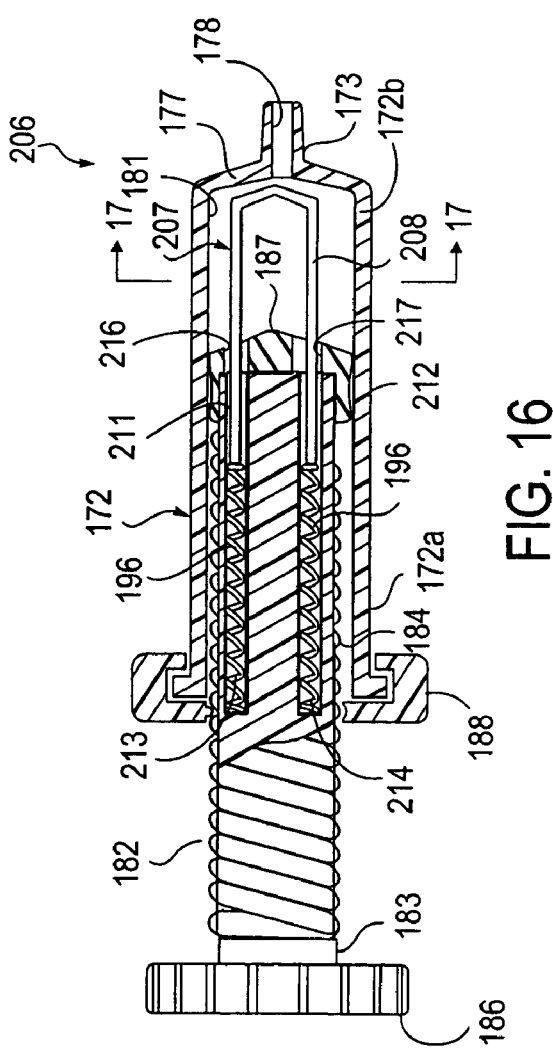

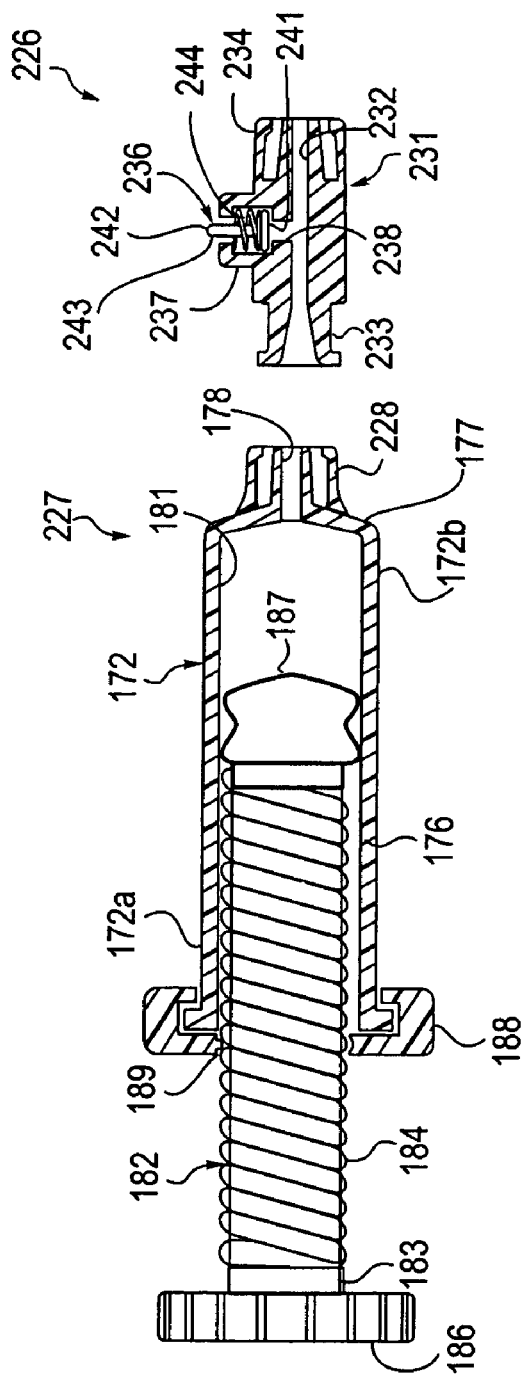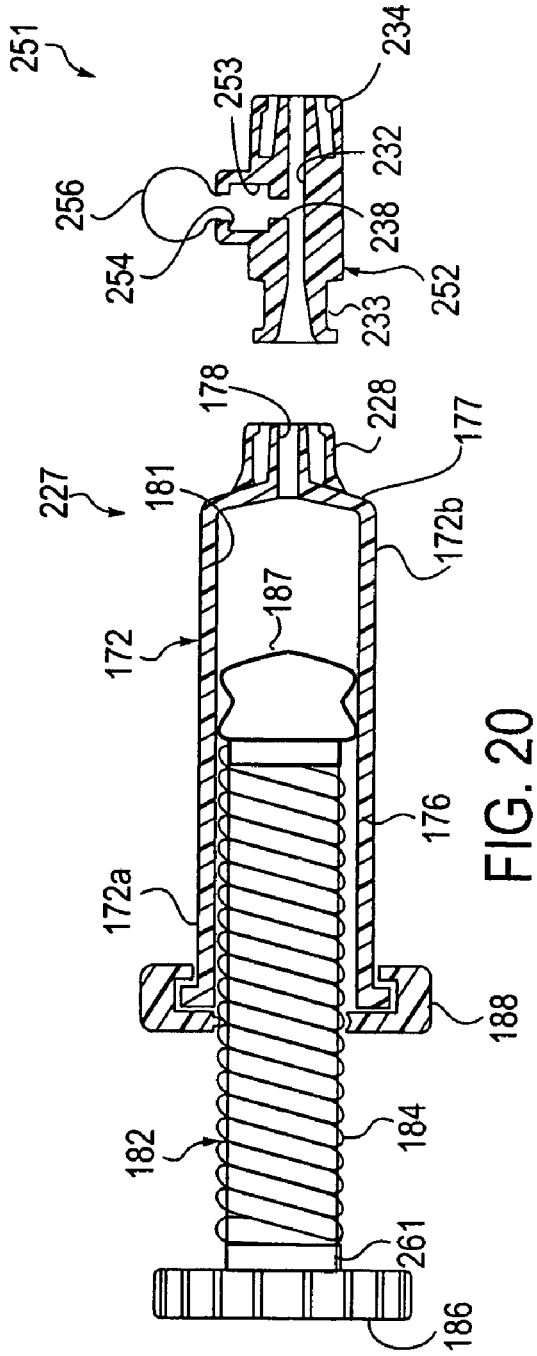

INJECTION DEVICE

SCOPE OF THE INVENTION

The present invention relates to medical devices and methods for treating a mammalian body and more particularly to medical devices and methods having injection needles.

BACKGROUND

Medical devices have been provided for the delivery of an implant-forming material to various portions of the wall forming a vessel such as the gastrointestinal tract of a mammalian body. See, for example, U.S. Pat. No. 6,251,063. There remains, however, a need for increased accuracy in the placement of such material and the implants formed thereby.

SUMMARY OF THE INVENTION

An injection device for use with tissue of a mammalian body comprising a first tubular member and a second tubular member slidably disposed in the first tubular member is provided. The first and second tubular members have respective proximal and distal extremities. The distal extremity of the second tubular member is provided with a needle that is extendable from the distal extremity of the first tubular member. The proximal extremity of the second tubular member is lockable relative to the proximal extremity of the first tubular member. The second tubular member has a column strength when locked within the first tubular member for limiting retraction of the second tubular member relative to the first tubular member during puncture of the tissue by the needle.

BRIEF DESCRIPTION OF THE DRAWINGS

The accompanying drawings, which are somewhat schematic in some instances and are incorporated in and form a part of this specification, illustrate several embodiments of the invention and, together with the description, serve to explain the principles of the invention.

FIG. 10 is a cross-sectional view of a further embodiment of an injection device for treating a mammalian body of the present invention in a first position.

FIG. 11 is a cross-sectional view of the injection apparatus of FIG. 10 in a second position.

FIG. 12 is a cross-sectional view of yet another embodiment of an injection device for treating a mammalian body of the present invention.

FIG. 13 is a cross-section view of a syringe for use with an injection device of the present invention.

FIG. 14 is a cross-sectional view of the syringe of FIG. 13 taken along the line 14-14 of FIG. 13.

FIG. 15 is cross-sectional view, similar to FIG. 14, of another embodiment of a syringe for use with an injection device for treating a mammalian body of the present invention.

FIG. 16 is a cross-sectional view of a further embodiment of a syringe for use with an injection device of the present invention.

FIG. 17 is a cross-sectional view of the syringe of FIG. 16 taken along the line 17-17 of FIG. 16.

FIG. 18 is cross-sectional view, similar to FIG. 17, of another embodiment of a syringe for use with an injection device for treating a mammalian body of the present invention.

FIG. 19 is a cross-sectional view of yet a further embodiment of an injection device for treating a mammalian body of the present invention.

FIG. 20 is a cross-sectional view of yet another embodiment of an injection device for treating a mammalian body of the present invention.

DESCRIPTION OF THE INVENTION

Figure 1:
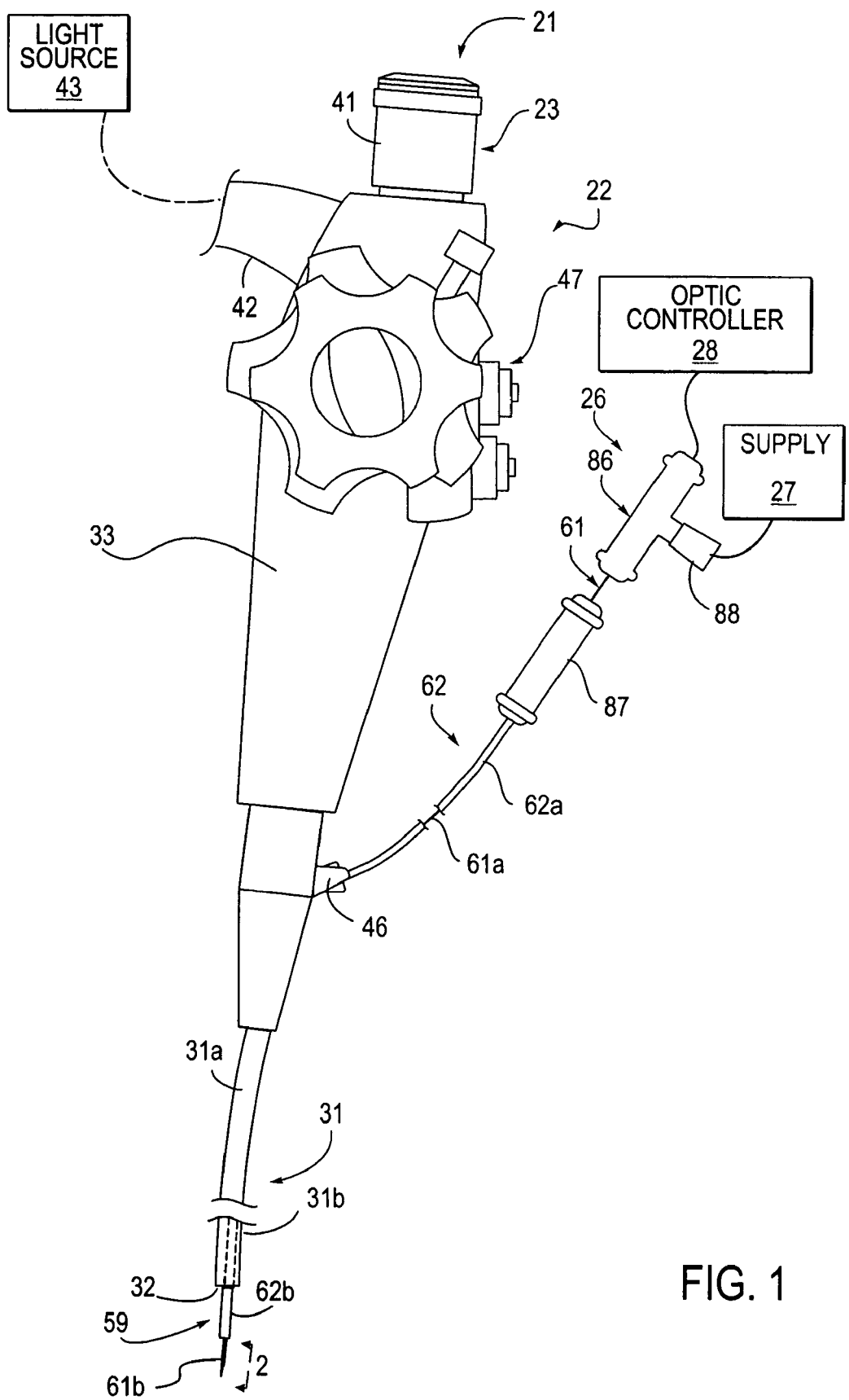
FIG. 1 is a plan view of a medical device utilizing an injection device for treating a mammalian body of the present invention.

The method of the present invention can be performed with an apparatus of the type shown in FIG. 1. Apparatus or medical device 21 shown therein includes a probe member or probe 22 having an optical viewing device 23. A needle assembly or injection device 26 is slidably carried by probe 22. Treatment device 21 further includes a supply assembly 27 and an optional optic controller 28 mounted to the proximal end portion of needle assembly 26.

A conventional or other suitable gastroscope or endoscope can be used for probe 22. The exemplary probe 22 includes a flexible elongate tubular member or insertion tube 31 having proximal and distal extremities 31a and 31b and a distal face 32. Insertion tube 31 has been sectioned in FIG. 1 so that only a portion of proximal extremity 31a and distal extremity 31b are shown. A handle means or assembly is coupled to proximal extremity 31a of the insertion tube 31 and includes a conventional handle 33. The tubular insertion tube 31 is provided with at least one bore and preferably a plurality of bores or passageways 36 extending from proximal extremity 31a to distal extremity 31b. A portion of one such passageway 36 is shown in FIG. 1.

Optical viewing device 23 is formed integral with probe 22 and has an optical element or objective lens (not shown) carried by one of the passageways 36 of the device 23. The objective lens has a field of view at distal face 32 which permits the operator to view forwardly of insertion tube distal extremity 31b. Optical viewing device 23 further includes an eye piece 41 mounted on the proximal end of handle 33. A connection cable 42, a portion of which is shown in FIG. 1, extends from handle 33 to a conventional light source 43. At least one light guide extends through cable 42 and insertion tube 31 for providing illumination forwardly of distal face 32 of the insertion tube 31.

One of the passageways provided in insertion tube 31 extends to a side port 46 formed in handle 33. Insertion tube 31 is flexible so as to facilitate its insertion and advancement through a body and is provided with a bendable distal end for selectively directing distal face 32 in a desired direction. A plurality of finger operable controls 47 are provided on handle 33 for, among other things, operating the bendable distal end of insertion tube 31 and the supply and removal of fluids through the insertion tube 31.

Injection device 26 is similar to a sclerotherapy needle and includes a stylet 59 having a needle member 61 provided with a proximal end portion or extremity 61a and a distal end portion or extremity 61b and an optional sleeve-member or sleeve 62 provided with a proximal end portion or extremity 62a and a distal end portion or extremity 62b. Sleeve or first elongate tubular member 62 is made from any suitable material such as flexible plastic or metal and has a lumen extending longitudinally therethrough for receiving the needle or second tubular member 61. The sleeve 62 and the needle member 61 are slidable relative to each other in a longitudinal direction. In this regard, needle member 61 is slidably disposed in sleeve 62 and movable between a retracted position in which the needle member is recessed within distal end portion 62b of sleeve and an extended position in which the needle member 61 projects distally of the sleeve 62. Needle member 61 and sleeve 62 can be slidably disposed within a passageway 36 and side port 62 of insertion tube 31 and each have a length so that when distal end portions 61b and 62b are extending from distal extremity 31b of the insertion tube 31 or otherwise in the vicinity of distal face 32, proximal end portions 61a and 62a are accessible at side port 46.

Figure 2:
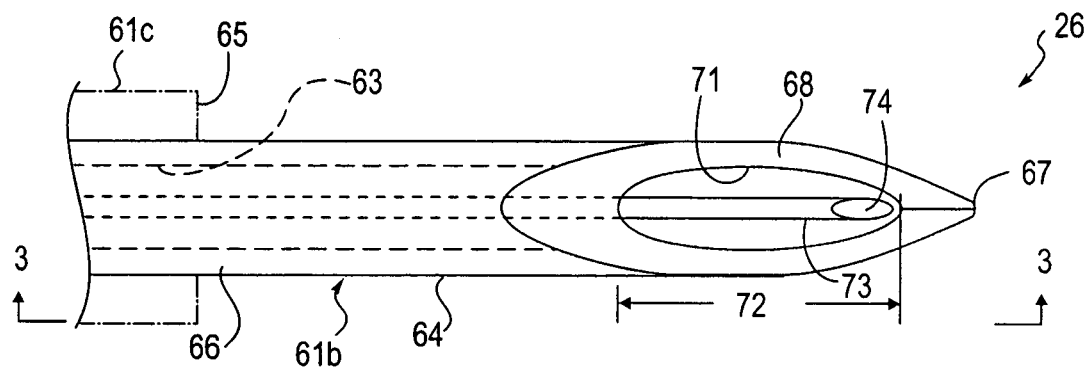
FIG. 2 is a top plan view of the distal extremity of the injection device of FIG. 1 taken along the line 2-2 of FIG. 1.
Figure 3:
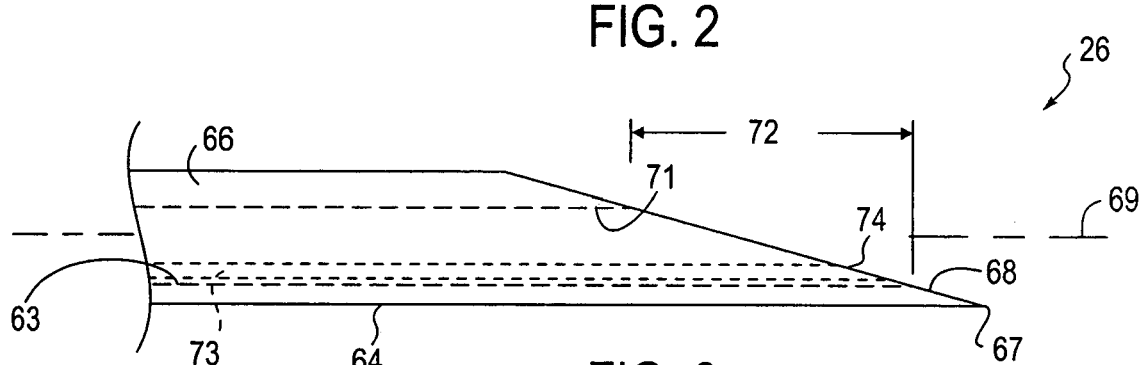
FIG. 3 is a side elevational view of the distal extremity of the injection device of FIG. 1 taken along the line 3-3 of FIG. 2.

The hollow or tubular needle member 61 has a lumen or passage 63 extending longitudinally therethrough from proximal end portion 61a to distal end portion 61b (see FIGS. 2-3). In one preferred embodiment of injection device 26, the proximal portion 61a and a central or elongate portion 61c of the needle member are made from flexible plastic tubing and the distal extremity 61b of the needle member is a slender tube or needle 64 made from metal, rigid plastic or any other suitable material. The central or elongate portion 61c of the needle member extends distally to a shoulder 65, shown in phantom lines in FIG. 2, from which needle 64 extends. The needle 64 is pressed into or otherwise suitably attached to the distal end of the elongate portion 61c of needle member 61. Metal needle 64 is preferably made from stainless steel and has a size ranging from 14 to 30 gauge, preferably ranging from 23 to 26 gauge and more preferably approximately 23 gauge. Where a 23 gauge needle 64 is provided, the internal diameter of needle bore 63 can range from 0.012 to 0.017 inch.

As shown most clearly in FIGS. 2-3, the needle 64 is formed by a cylindrical wall 66 and has a sharpened or beveled distal tip 67 formed in part by a tapered end surface 68 preferably lying in a plane. The tapered end surface 68 extends at an angle ranging from 10° to 40°, and preferably approximately 15°, relative to the longitudinal axis 69 of the needle 64. At least one opening 71 is provided in needle 64 and can include or consist of an opening 71 provided in tapered end surface 68. Although needle opening 71 can be of any suitable shape, the illustrated opening 71 in tapered end surface 68 of needle has a longitudinal dimension or length 72 of approximately two millimeters.

Injection device 26 is preferably further provided with one or more optic elements 73, preferably in the form of an optical fiber 73 for viewing and/or analyzing the tissue being treated (see FIGS. 2-3). Each of the elements 73 terminates at a distal face 74 preferably lying in a plane. For simplicity, only one optical element or fiber 73 is shown in the drawings. The one or more optic elements 73 are preferably carried internal of the injection device 26 and, for example, can be carried by the sleeve 62, needle member 61, between the sleeve 62 and the needle member 61 or in any other suitable manner. When carried by the needle member 61, the optic element(s) 73 can be carried by needle 64 or between the needle 64 and the flexible tubing forming the proximal extremity 61a of the needle member 61. In one preferred embodiment, illustrated in the drawings with respect to one optic element 73, the central passageway or internal lumen 63 of the needle member 61, including needle 64 thereof, is sized to receive the optic element 73. Passageway 63, as discussed above, further serves as the flow path for the material being injected by the injection device 26. Although the distal end of optic element 73 is shown as extending to the distal end of opening 71 and having a distal face 74 inclined at an angle approximating the inclination angle of tapered surface 68, and for example lying in the plane of the tapered surface 68, the optic element or fiber 73 can instead extend only to the proximal end of the opening 71 or elsewhere within needle 64, and can have a distal face perpendicular to the length of the fiber 73 or inclined at any other angle. Where two optic elements 73 are provided, one element 73 can be for transmitting light distally of the needle 64 and the second element 73 can be provided for transmitting proximally through such element 73 reflected or other light traveling proximally towards the needle.

Figure 4:
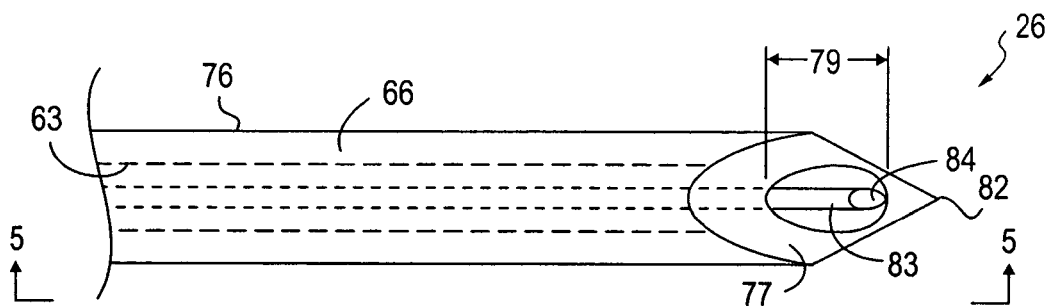
FIG. 4 is a top plan view, similar to FIG. 2, of a distal extremity of another embodiment of an injection device for treating a mammalian body of the present invention.
Figure 5:
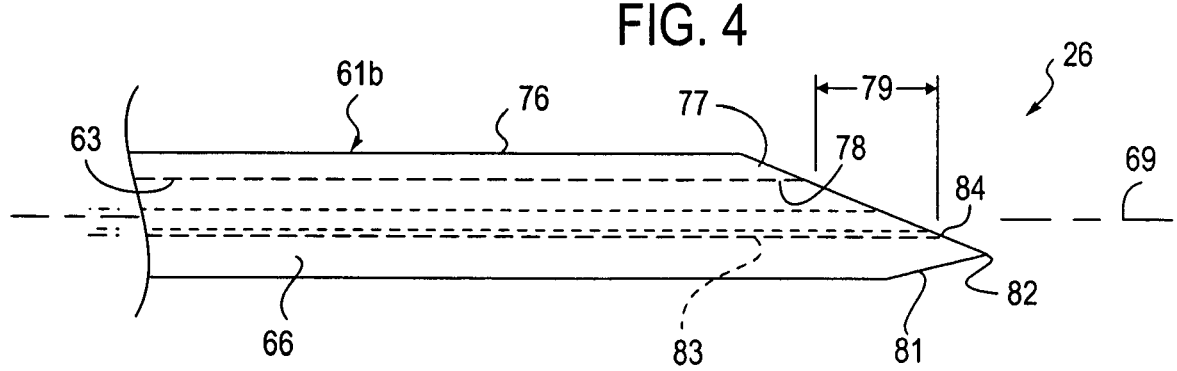
FIG. 5 is a side elevational view, similar to FIG. 3, of the distal extremity of the injection device of FIG. 4 taken along the line 5-5 of FIG. 4.
Figure 6:
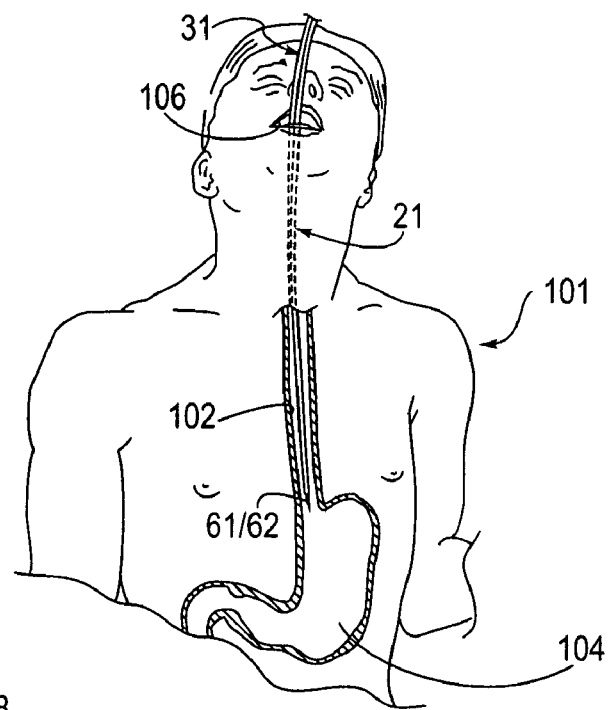
FIG. 6 is an enlarged elevational view of the medical device of FIG. 1 in a portion of a passageway of a mammalian body.
Figure 7:
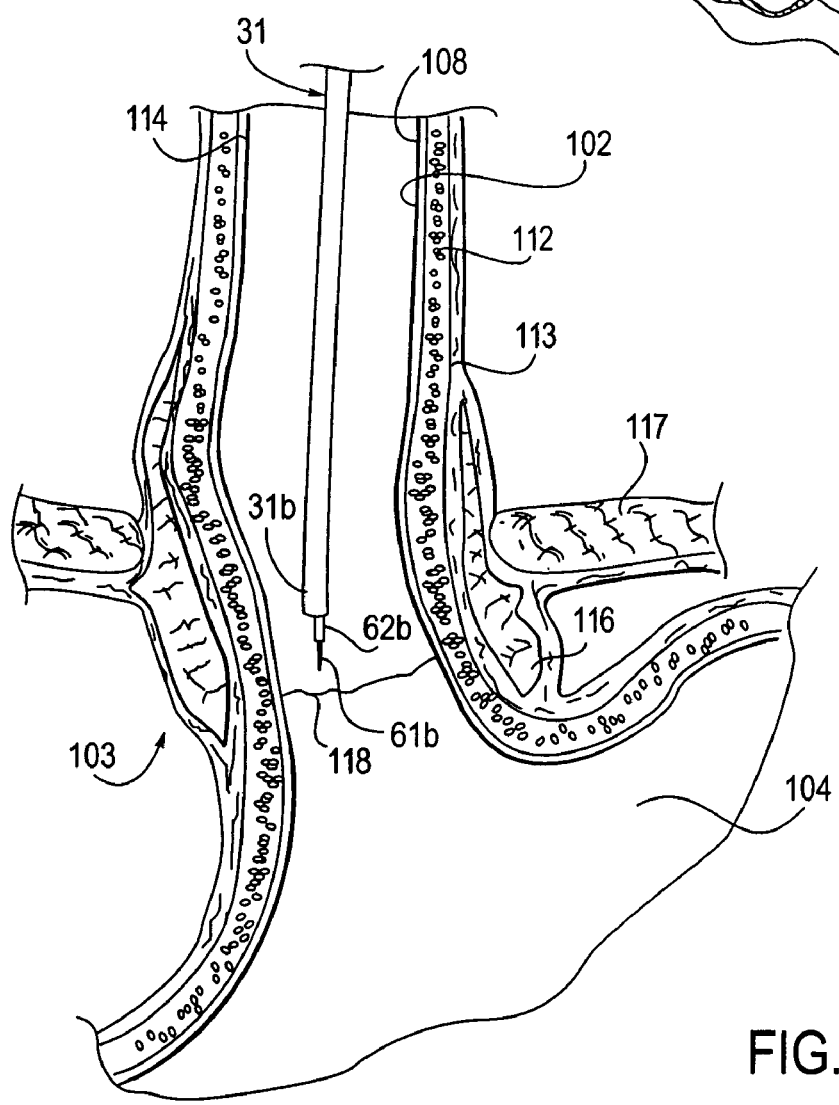
FIG. 7 is a still further enlarged view of the medical device of FIG. 1 in a portion of a passageway of a mammalian body.

In another embodiment of injection device 26, a needle 76 is provided at the distal extremity of needle member 61 (see FIGS. 4 and 5). Needle 76 is substantially similar to needle 64 and like reference numerals have been used to describe like components of needles 76 and 64. The needle 76 is provided with a first tapered distal surface 77, preferably lying in a plane, and is provided with an oblong opening 78 in the surface 77. Surface 77 is inclined at an angle ranging from 10° to 45°, preferably greater than 25° and more preferably approximately 30° relative to the longitudinal axis 69 of needle 76. Opening 78 has a longitudinal dimension 79 of approximately one millimeter for a 23 gauge needle 76. Needle 76 can optionally have a reverse bevel provided by second tapered distal surface 81, preferably lying in a plane, which is tapered at an angle ranging from 10° to 20° and preferably approximately 14° relative to the longitudinal axis 69 of needle 76 and can extend along the longitudinal length of the needle 76 a distance ranging from 0.2 to two millimeters and preferably approximately one millimeter. First and second tapered surfaces 77 and 81 meet to form a sharpened distal tip 82 which is pointed to facilitate tissue penetration.

Injection needle 76 may also be provided with at least one optic element substantially similar to the at least one optic element 73 of needle 64. As illustrated in FIGS. 4 and 5, needle 76 is provided with at least one optic element 83 having a distal face 84. Optic element 83 extends through lumen 63 of needle 76 and, as shown in the illustrated embodiment, distal face 84 lies in the plane of tapered end surface 77 of the needle 76 and has an inclination or bevel angle relative to longitudinal axis 69 that approximates the inclination angle of needle 76. More specifically, end surface 84 has an angle ranging from 10° to 45°, preferably greater than 25° and more preferably approximately 30° relative to the longitudinal axis 69 of needle 76. Similar to needle 64, the needle 76 can be provided with two optic elements 83, one element 83 can be for transmitting light distally of the needle 76 and the second element 83 can be provided for transmitting proximally through such element 83 reflected or other light traveling proximally towards the needle 76.

A fluid connector 86 is secured or coupled to proximal end portion 61a of needle member 61 and a gripping member or grip 87 is secured to the proximal end portion 62a of the sleeve 62 (see FIG. 1). Fluid connector 86 includes at least one luer fitting portion 88, or any other suitable fitting portion, which communicates with the passageway 63 in needle 61. Supply or reservoir 27 is coupled to the proximal extremity of injection device 26, and preferably to the proximal extremity 61a of needle member 61, and can be of any suitable type. For example, one or more syringes (not shown) for containing an injectable material, or the ingredients thereof, of the present invention can be included in supply 27. The supply 27 is included within the means of medical or treatment device 21 for introducing at least one liquid, solution, composition or material through passage 63 of needle 61 and out one or more of the openings 71 provided in the distal extremity 61b of needle member 61.

Fluid connector 86 and grip 87 are longitudinally movable relative to each other so as to cause relative longitudinal movement between needle member 61 and sleeve 62. More specifically, grip 87 can be slid forwardly and rearwardly on proximal end portion 61a of the needle 61 relative to fluid connector 86. Movement of grip 87 forwardly relative to fluid connector 86 causes distal end portion 62b of sleeve 62 to extend fully over distal end portion 61b of the needle member 61 so that the needle has fully retracted within sleeve 62. Conversely, movement of grip 87 rearwardly relative to fluid connector 86 causes sleeve distal end portion 62b to retract relative to needle distal end portion 61b so as to expose needle 64 of distal end portion 61b.

Exemplary injectable materials or compositions which can be included in supply 27 and thus utilized in the method and apparatus of the present invention include any suitable material or composition from which an implant can be formed when a fluid, separately or in conjunction with another fluid, is introduced into the tissue of a body. Although aqueous or nonaqueous solutions are among the fluids that can be used, an inert, nonresorbable material is preferred. Preferred nonaqueous solutions are any of the solutions disclosed in International Application No. PCT/US99/29427 filed Dec. 10, 1999, the entire content of which is incorporated herein by this reference. One such injectable or implant-forming material comprises at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a solution which can be introduced into the body as a liquid and from which a solid thereafter precipitates or otherwise forms. A preferred embodiment of such a solution is a solution of a biocompatible composition and an optional biocompatible solvent which can further optionally include a contrast agent for facilitating visualization of the solution in the body. The solution can be aqueous or nonaqueous. Exemplary biocompatible compositions include biocompatible prepolymers and biocompatible polymers.

A particularly preferred implant forming solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 µm or less. It should be appreciated that any percents stated herein which include a contrast agent would be proportionally adjusted when the contrast agent is not utilized.

Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly(C1-C6) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly (C1-C6) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 µm or less. Other water insoluble contrast agents include gold, tungsten and platinum powders. Methods for preparing such water insoluble biocompatible contrast agents having an average particle size of about 10 µm or less are described below. Preferably, the contrast agent is water insoluble (i.e., has a water solubility of less than 0.01 mg/ml at 20° C.)

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the non-aqueous solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 µm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm).

When the prepolymer is liquid (as in the case of polyurethanes), the use of a biocompatible solvent is not absolutely necessary but may be preferred to provide for an appropriate viscosity in the nonaqueous solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Specific embodiments of nonaqueous solutions suitable for use in the apparatus and methods of the invention are described in U.S. Pat. No. 5,667,767 dated Sep. 16, 1997, U.S. Pat. No. 5,580,568 dated Dec. 3, 1996 and U.S. Pat. No. 5,695,480 dated Dec. 9, 1997 and International Publication Number WO 97/45131 having an International Publication Date of Dec. 4, 1997, the entire contents of which are incorporated herein by this reference.

Other suitable implantable materials include any material capable of being delivered through a needle, solutions, suspensions, slurries, biodegradable or nonbiodegradable materials and two part or other mixtures. Exemplary implantable materials include injectable bioglass as described in Walker et al., "Injectable Bioglass as a Potential Substitute for Injectable Polytetrafluorethylene Particles", J. Urol., 148:645-7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg, biocompatible compositions comprising carbon coated beads such as disclosed in U.S. Pat. No. 5,451,406 to Lawin, collagen and other biodegradable material of the type disclosed in U.S. Pat. No. 4,803,075 to Wallace et al., biocompatible materials such as disclosed in U.S. Pat. No. 6,296,607 to Milbocker, U.S. Pat. No. 6,524,327 to Spacek, and U.S. Publication Nos. 2002/0049363 and 2003/0135238 to Milbocker, and other known injectable materials.

Optic controller 28 is coupled to the proximal end of the optical fiber(s) 73 for supplying light to the one or more fibers, sensing light transmitted back by one or more of the fibers 73 and otherwise controlling the optical performance of the one or more optical elements or fibers 73. Controller 28 is shown in FIG. 1 as being coupled to the optic elements or fibers by means of fluid connector 86.

To assist in describing the utilization of the devices and practice of the method of the present invention, a portion of a mammalian body, in this case a human body 101, is shown in FIGS. 6-9. Body 101 has an internal cavity in the form of the passage of the esophagus 102 extending through a lower esophageal sphincter 103 to a stomach 104. Such cavity is accessible by a natural body opening in the form of mouth 106 and is defined by a wall 107. Esophagus 102 is part of the gastrointestinal tract of body 101 that extends from mouth 106 to an anus (not shown). The esophageal mucosa 108 serves as the inner layer of the intraluminal wall 107 in the esophagus 102. Wall 107 has a muscle layer comprising layer of circular muscle 112 extending beneath mucosa layer 108 and layer of longitudinal muscle 113 beneath circular muscle 112. The muscle layers 112 and 113 each extend around the esophagus 102 and the stomach 104. Wall 107 further includes a submucosal layer or submucosa 114 extending between mucosa 108 and muscle layers 112 and 113. A submucosal space, that is a potential space, can be created between submucosa 114 and circular muscle layer 112 by the separation of layer 108 from muscle layer 112. In addition, as with any muscle, wall 107 includes an intramuscular potential space, that is a space which can be created intramuscularly by distension and separation of muscle fibers within a single muscle. Wall 107 has a depth or thickness which includes at least mucosal layer 108, submucosal layer 114, circular muscle layer 112 and longitudinal muscle layer 113. The phreno-esophageal ligament 116 and diaphragm 117 extend around the esophagus 102 above the lower esophageal sphincter 103. In the vicinity of the lower esophageal sphincter, as that term is used herein, includes at least the lower third of the esophagus 102, the squamous columnar junction 118, and the gastric cardia or upper portion of the stomach 188.

Although medical device 21 can be used in any number of procedures, in one preferred procedure the device is introduced into a natural body opening to access a vessel in the body, whether a passageway or an organ. In a further preferred procedure, device 21 can be utilized to deliver of a fluid, composition or other material to a wall of a passageway within a mammalian body to treat the body and more particularly to the wall forming the gastrointestinal tract of a mammalian body. Particularly preferred procedures are described in U.S. Pat. Nos. 6,231,613, 6,234,955, 6,238,335, 6,248,058, 6,251,063, 6,251,064, 6,358,197, 6,540,789 and 6,595,910, the entire content of each of which is incorporated herein by this reference. The exemplary procedure utilized for describing the devices and methods of the present invention is the treatment of gastroesophageal reflux disease.

In operation and use of medical device 21 having injection device 26 in the method of the present invention, more fully described in U.S. Pat. No. 6,251,063, supply 27 is filled with an appropriate material in preparation of the procedure and coupled to the proximal extremity of needle member 61 by means of fluid connector 86. Optic controller 28 is also coupled to the proximal extremity of the needle member, for example by means of fluid connector 86. Probe 22 is prepared by connecting light cable 42 to light source 43 and attaching the proper eye piece 41 to handle 33. In addition, all other conventional attachments are applied to probe 22.

After the patient has been appropriately sedated or anesthetized, probe handle 33 is grasped by the physician to introduce distal extremity 31b of probe 22 into mouth 106 and advance insertion tube 31 down esophagus 102 to the vicinity of the lower esophageal sphincter 103. Insertion tube 31 has a length so that when distal extremity 31b is in the vicinity of the tissue being treating, in this case in the vicinity lower esophageal sphincter 103, proximal extremity 31a is outside of body 101.

The distal end portions or extremities 61b and 62b of injection device 26 are now inserted though side port 46 of insertion tube 31 and advanced until such end portions are in the vicinity of distal extremity 31b of the insertion tube 31. Needle 61 and sleeve 62 are each movable between a first position in which distal end portions 61b and 62b are each retracted within insertion tube 31, and thus recessed within passageway 36 of the insertion tube, and a second position in which distal end portions 61b and 62b extend distally beyond the distal end of insertion tube 31. The needle 61 and sleeve 62 each have a sufficient length so that the physician can extend them distally from the end of insertion tube 31 a significant distance, should that be desired. Distal extremity 31b of the insertion tube 31 is shown in the vicinity of lower esophageal sphincter 103 and FIGS. 6 and 7. Both needle member 61 and sleeve 62 have been extended from distal extremity 3b and fluid connector 86 has been moved relative to grip 87 so as to advance needle 64 distally beyond extremity 62b of the sleeve 62.

The physician cases sharpened tip 67 of needle 64 to penetrate wall 107 by moving needle member 61 and sleeve 62 closer to side port 46. The field of view of optical viewing device 23 permits the physician to observe the penetration of wall 107. Thereafter, the physician causes an appropriate amount of injectable material to be introduced through needle 64 and into wall 107 to form at least one implant (not shown) in the wall. The injectable material can be deposited into any or all of the layers of wall 107, including between any of such layers. The implant can be of any suitable shape, for example an arcuate implant which extends around a portion or all of the wall as disclosed in U.S. Pat. No. 6,251,064. The implants can serve to augment the wall, bulk the wall, reduce the dispensability of muscle layers 112 and/or 113 of the wall, or serve any other purpose for treating the wall. When the ailment being treated is gastroesophageal reflux disease, the implant can serve to increase the competency of the lower esophageal sphincter 103.

A 23 gauge needle 64 is preferred to mitigate the possibility of a tear in the mucosal surface of the wall 107. Such a tear can result in splash back through the hole created by the needle and when exposed to an injectable or other material can result in sloughing of the entire mucosal surface. In addition, in a non-sterile environment such as the gastrointestinal tract, large mucosal tears are more prone to infection.

Figure 8:
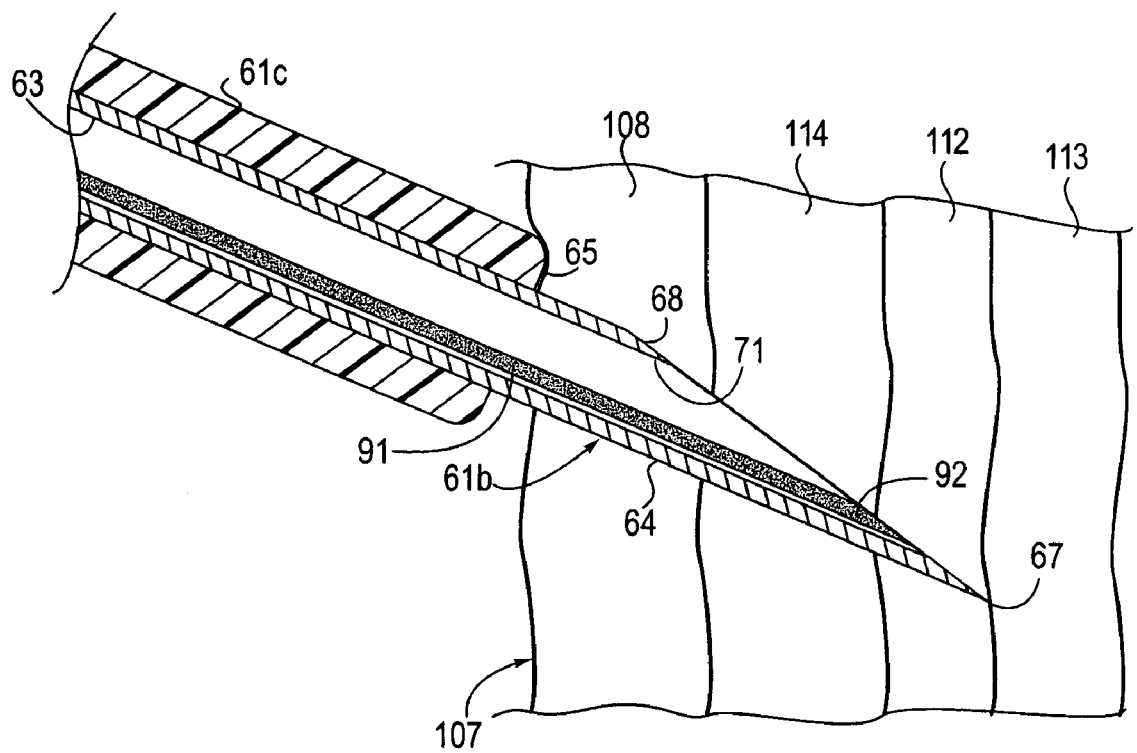
FIG. 8 is a cross-sectional view of the distal extremity of the injection device of FIG. 2 penetrating tissue in a passageway of the mammalian body.

Placement of needle 64 in wall 107, and thus introduction of the injectable material from the needle 64 into the wall 107, is facilitated by the predetermined sizing of the exposed portion of needle 64 relative to shoulder 65 of central portion 61c (see FIG. 8). More specifically, the length of the exposed portion of needle 65 is sized so that when shoulder 65 abuts wall 107, needle opening 71 is at the desired location within the wall 107. In this manner, the accuracy of material placement and resulting implant formation is enhanced.

Figure 9:
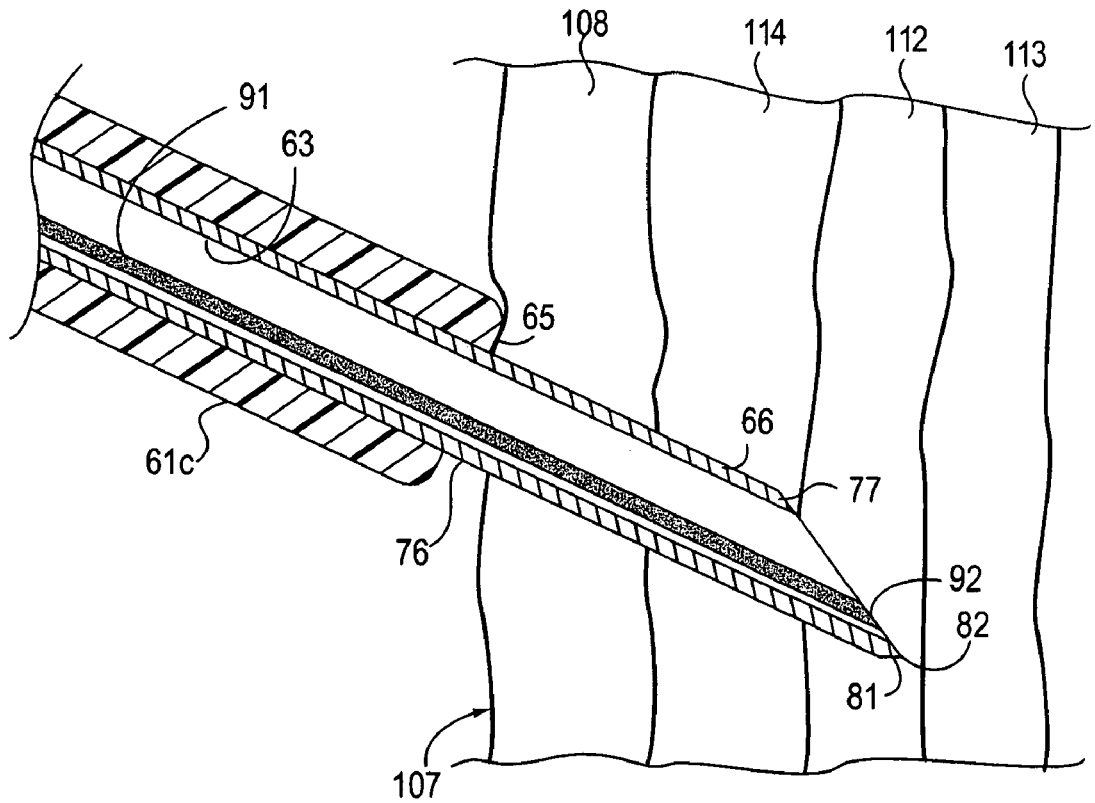
FIG. 9 is a cross-sectional view, similar to FIG. 8, of the distal extremity of the injection device of FIG. 4 penetrating tissue in a passageway of the mammalian body.

The placement of the injectable material within wall 107 is further enhanced when the inclination angle of the tapered end surface of the needle is increased relative to the longitudinal axis 69 of the needle. In this regard, and as is illustrated in FIGS. 2-5, increasing the inclination angle of the distal face of the needle reduces the longitudinal dimension or length of the distal opening in the needle. As discussed above, distal face 68 of needle 64 has an inclination angle of approximately 15° and a resulting opening 71 with a length 72 of approximately two millimeters. In comparison, distal face 77 of needle 76 has a relatively larger inclination angle of approximately 30° relative to longitudinal axes 69 resulting in distal opening 78 having a smaller length 79 of approximately one millimeter. As can be seen in FIG. 9, the relatively small length of opening 77 results in such opening 77 communicating with only one layer of wall 107—in this case circular muscle layer 112. In comparison, relatively long opening 71 of needle 64 communicates with mucosal layer 108, submucosal layer 114, and the circular muscle layer 112. Where the targeted tissue for the needle 64 or 76 is, for example, the muscle layer of the esophagus 102, which is approximately two to three millimeters thick, a needle opening having a relatively large longitudinal dimension can make placement of the material in the muscle layer difficult. As can be seen, the area though which the injected material is distributed can depend on the bevel angle at the distal end of the needle and the diameter of the needle. Enhancing the placement accuracy of the needle serves to inhibit damage to the mucosal layer and other adjacent muscle layers from improperly placed material.

The at least one optical element 73 or 83 of respective needle 64 and 76 permits the type of tissue into which the distal end of the needle is disposed to be determined, for example by interrogating the tissue spectrographically or spectrometrically. Where a single optical element is provided in the needle, light from optic controller 28 can be directed through the at least one optical element or fiber onto the tissue and reflected light received by the same at least one optical fiber and returned to the controller 28. Where first and second optical elements or fibers are provided, one fiber serves to shine light onto the tissue and the other fiber serves to receive the light reflected back by the tissue and transmit such reflected light to controller 28. A spectrometric analysis of the reflected light permits the type of tissue in the field of the optic elements to be distinguished. When evaluating the lower esophageal sphincter 103, for example, one goal is to differentiate whether the needle is within the esophageal mucosal 108 or submucosa 114 of the wall 107 or whether the needle is within one or more of muscle layers 112 and 113 by interrogating the tissue in the vicinity of the needle to detect the presence of myoglobin or hemoglobin or to determine the amount of oxygen saturation or light reflection or brightness. The beveled distal faces 74 and 84 of respective needles 64 and 76 provide less scatter and thus enhance the ability to spectrographically, spectrometrically or otherwise identify tissue. Where, as discussed above, the distal face 84 of optical element 83 is disposed at the proximal end of needle opening 78, the approximate 30° bevel at the distal end of needle 76 and the accompanying reduction in the longitudinal length 79 of opening 78 serves to reduce the longitudinal spacing between the distal end of the opening 79 and distal end viewing face 84 of the one or more optical elements 83 and thus permits more accurate identification of the tissue into which the injectable material from needle 76 is being placed.

Other embodiments of the injection device of the present invention can be utilized with medical device 21. In this regard, for example, an injection device 126 having a second tubular member slidably disposed within a first tubular member and having a column strength for limiting retraction of the second tubular member relative to the first tubular member during the operation of the device 126 is provided. Injection device 126 is similar in many respects to injection device 26 described above and like reference numerals have been used to described like components of injection devices 126 and 26. More specifically, injection device 126 has a first tubular member or sleeve 127 having a proximal extremity or end portion 127a and distal extremity or end portion 127b. The sleeve 127 is made from plastic or any other suitable material and is provided with a distal opening 128. The proximal extremity 127a of the sleeve has a sufficient thickness so as to be relatively rigid and is provided with an inner conical surface 129 forming a recess 130. A longitudinally-extending passage 131 extends from recess 130 through sleeve 127 to distal opening 128.

The second tubular member of injection device 126 can be in the form of a needle member or assembly 132 having a proximal end portion or extremity 132a, a distal extremity or end portion 132b and a central or tube portion 132c. Needle assembly 132 can be formed from a cylindrical tube made from any suitable metal such as stainless steel. Alternatively, needle assembly 132 can have a construction similar to needle member 61 described above and, as such, proximal extremity 132a and central portion 132c can be made from plastic or any other suitable material. Central portion 132c terminates at a shoulder 133. In this embodiment of needle assembly 132, illustrated in FIGS. 10 and 11, distal extremity 132b can include tubular needle 64 pressed into the distal end of central portion or inner tube 132c at shoulder 133. As disclosed above, the metal tube or needle 64 is provided with an internal passage 63 extending longitudinally therethough and a tapered end surface 68 terminating at sharpened tip 67. Proximal extremity 132a of the needle assembly includes a hub 134, preferably formed integral with central portion 132c and made from plastic or any other suitable material. Hub 134 includes a conventional fitting 136 for permitting fluid coupling to the needle assembly 132. A fluid passageway 137 extends longitudinally through needle assembly 132 and includes at its distal end portion passage 63 of needle 64.

Needle assembly 132 is movable between a first position, shown in FIG. 10, in which needle 64 is recessed within distal opening 128 of the sleeve 127 and hub 134 is disengaged from needle proximal extremity 127a, and a second or extended position, shown in FIG. 11, in which needle 64 and optionally the distal end of central portion 132c extends beyond the distal opening 128 of sleeve 127 and hub 134 is locked within recess 130 of the flared proximal extremity 127a of the sleeve 127.

Means can be carried by the proximal extremities of the needle assembly 132 and the sleeve 127 for locking proximal extremity 132a of the needle assembly 132 with proximal extremity of 127a of the sleeve or sheath 127. Such means can include hub 134, which is provided with an outer conical ends surface 138 at its distal end which removably seats or locks against inner conical surface 129 of sleeve proximal extremity 127a. The outer conical surface 138 has a taper or configuration which cooperatively matches the taper or configuration of inner conical surface 129. In the preferred embodiment illustrated in FIGS. 10 and 11, outer conical surface 138 is inclined relative to the longitudinal axis of injection device 126 at the same angle as inner conical surface 129 is inclined relative to such longitudinal axis. The flared proximal extremity 127a of the sleeve 127 preferably expands slightly under pressure, and hence the hub 134 can be pressed into recess 130 and locked by the friction fit of outer conical surface 138 with inner conical surface 129.

Central portion 132c of the needle assembly of 132 is provided with a sufficient column strength so that such central portion or tube 132c does not buckle when axial forces are exerted on shoulder 132 or needle 64 extending from such shoulder. In addition, the outer diameter of central portion 132c of tube 132c preferably closely approximates the inner diameter of sleeve 127 so that bending or buckling of central portion 132 within the sleeve 127 is inhibited.

One or more optic elements can be included in injection device 126, for example disposed in passageway 137 and passage 63 in the manner described above with respect to injection device 26, for interrogating tissue or other purposes.

In operation and use, injection device 126 is introduced into probe 22 in a manner similar to that described above with respect to injection device 26. Supply 27 is coupled to injection device 126, and preferable proximal extremity 132a of the needle assembly 132, for providing a supply of a suitable injectable material to the device 126. Where one or more optic elements are included within the injection device 126, optic controller 28 can be utilized.

Although injection device 126 can be used with probe 22 in any of the procedures discussed above, the operation of the device 126 will be described in connection with the treatment of gastroesophageal reflux disease. In such a procedure, distal extremity 31b of insertion tube 31 is desirably positioned within the esophagus 102. Either before or after sleeve distal extremity 127b is extended from insertion tube passageway 36, needle 64 is extended from distal opening 128 by pressing hub 134 into recess 130 and locking the outer conical surface 138 of the hub against the inner conical surface 129 of recess 130. Needle 64 is then guided by tube distal extremity 31b to a location adjacent to the tissue to be treated and, thereafter, pressed against wall 107 so as to penetrate the wall. The injectable material from supply 27 is then introduced by the needle 64 into the appropriate layer of wall 107 so as to treat the wall. The high column strength of central portion 132c of the needle assembly 132 and the relatively close spacing between the outer cylindrical surface of the central portion 132c and the inner cylindrical surface of sleeve 127 inhibits buckling of the needle assembly 132 and thus causes distal extremity 132b of the needle assembly 132 to travel essentially one-for-one with the proximal extremity 132a of the needle assembly 132.

Once a suitable injection has been made within the first target site, needle 64 can be withdrawn from the wall 107 and thereafter utilized to penetrate another portion of wall 107. An additional injection of material can be made in such other wall portion. As can be appreciated, repeated injections can be made at various walls sites to, for example, create a desirable pattern or configuration of implants within the wall.

The limiting of the longitudinal travel or retraction of needle 64 relative to sleeve 127 permits greater accuracy in the placement depth of the needle 64 in the targeted tissue, thus facilitating relatively consistent puncture depths between injection sites. In each such wall penetration, the depth of needle penetration into the wall 107 can be determined by observing the amount that the proximal extremity of the injection device 126, for example, proximal extremity 132a of needle assembly 132, advances into port 46 of probe 22. Since contraction of the needle assembly 132 has been limited by the increased column strength of the needle assembly 132 and the relative sizing of central portion or tube 132c and sleeve 127, the amount of the advancement of the needle assembly 132 into the probe 22 translates essentially one-to-one with the amount that needle 64 is advanced into the tissue of wall 107.

Needle assembly 132 of injection device 126 can be withdrawn from sleeve 127 while the sleeve is disposed within insertion tube 31 and the probe is disposed within the patient's body. One advantage of being able to withdraw needle assembly 132 proximally from sleeve 127 is to facilitate cleaning of passage 131 in sleeve 127 during use of the injection device 126. For example, should the injectable material being supplied through the needle assembly 132 undesirably clog sleeve passage 137 while the injection device 126 is disposed within probe 22 in situ, needle assembly 132 can be withdrawn from sleeve 127 while the sleeve remains within probe 22. Thereafter, passage 131 of the sleeve 127 can be cleared of any undesirable injectable material that has accumulated therein. In one preferred procedure for so cleaning sleeve 127, a supply of a suitable biocompatible solvent or other fluid is coupled to proximal extremity 127a of the sleeve 127 and applied under pressure to passage 131 so as to clear or clean the passage of undesirable injectable material therein. Thereafter, the solvent or fluid supply can be decoupled from sleeve 127, and needle assembly 132 reintroduced into sleeve passage 131 for continuing the treatment procedure.

In another embodiment of the invention, a side port may be provided on the injection device for facilitating the cleaning of any injectable material that may have undesirably accumulated within the sleeve. In this regard, an injection device 151 having similarities to injection device 126 is illustrated in FIG. 12, wherein like reference numerals have been used to describe like components of injection devices 151 and 126. As shown therein, sleeve or sheath 127 has an internal passage 152 extending from recess 130 to distal opening 128 for receiving needle assembly 132. A port 153 is formed in the side of outer sleeve 127 adjacent to sleeve proximal extremity 127a for providing secondary access to passage 152. The side port 153 includes a conventional fitting 156 and a bore or passageway 157 extending from the fitting 156 to longitudinal passage 152 of the sleeve or sheath 127.

The radial spacing between the outer surface of central portion or inner tube 132c of the needle assembly 132 and the inner surface of sleeve 127 is greater than the corresponding spacing in injection device 126 to more easily permit fluid travel between the needle assembly 132 and sleeve 127 and injection device 151. A suitable fluid seal is disposed between needle assembly 132 and sleeve 127 proximal of side port 153 for inhibiting undesirable fluid travel between the port and recess 130. One exemplary such fluid seal is O-ring 158 made of any suitable material such as rubber disposed within an angular groove 159 formed in the inner surface of sleeve 127 proximal of side port 153 and distal of recess 130. A reservoir of any suitable flushing fluids such as a suitable solvent can be fluidly coupled to fitting 156 of side port 153 for permitting the solvent to be introduced into the annular space between the needle assembly 132 and sleeve 127.

In operation and use, injection device 151 can be utilized with probe 22 in a manner similar to that described above with respect to injection device 126. If injectable material should clog or partially obstruct sleeve passage 152 during the procedure, a solvent, and preferably a biocompatible solvent, may be introduced through side port 153 for flushing or otherwise cleaning out any of the injectable material that may have accumulated within sleeve passage 152. In one specific application of injection device 151, a nonaqueous solution is introduced by needle 64 into wall 107 of the gastrointestinal tract of a mammalian body to form implants in the wall. More specifically, at least one nonaqueous solution can be introduced into the wall 107 to form a nonbiodegradable solid in the wall. In one preferred embodiment, the at least one solution is a solution of a biocompatible polymer and a biocompatible solvent and the forming step includes precipitating the biocompatible polymer from the solution so that biocompatible polymer solidifies in the wall. Should any of the biocompatible polymer in the nonaqueous solution solidify or precipitate within injection device 151, for example within outer sleeve 127, such material may effectively plug sleeve 127 so that needle 64 may not be deployed from sleeve distal opening 128. In order to clear sleeve 127 for use, a solvent such as dimethylsulfoxide (DMSO) can be introduced through side port 153 under pressure to redissolve the biocompatible polymer at the point of precipitation and thus clear sleeve 127 for use.

In another embodiment of the invention, a threaded syringe can be included in medical device 21 for coupling to any of the injection devices described above and for supplying an injectable material, or a portion thereof, to a body of a patient. Threaded syringe 171 shown in FIGS. 13-15 has a body or housing 172 provided with an open proximal end portion 172a and a distal end portion 172b terminating at a suitable coupling or fitting 173. The housing 172, made from any suitable material such as plastic, includes a cylindrical sidewall 176 joined to a distal or end wall 177 which tapers to an opening of a passage 178 extending through fitting 173. Sidewall 176 and end wall 177 form a chamber 181 within housing 172 for containing a suitable fluid such as the injectable material of the present invention. A plunger 182 is provided for forcing the injectable material from chamber 181 out through supply passage 178. The elongate plunger 182 is made from plastic or any other suitable material and includes a cylindrical or central portion 183 having external treads 184 extending therealong. A twist knob 186 is formed at the proximal end of the plunger 182. A piston seal 187 made from any suitable elastic material such as rubber is mounted on the distal end of the cylindrical body for sealably engaging the internal surface of housing sidewall 176 as the plunger 182 advances into the housing. A threaded collar 188 is mounted on the proximal end of syringe housing 172 and is provided with internal threads 189 for engaging the external threads 184 of plunger body 183.

A mixing member or mixer 192 can be carried by plunger 182 for mixing the injectable material disposed within chamber 181 during threaded advancement or retraction of the plunger 182 relative to housing 172. In this regard, an elongate bore 193 extends longitudinally through the distal end of plunger body 183. Piston seal 187 has an opening 194 for permitting the bore 193 to communicate with chamber 181. The mixer or mixing rod 192 extends though opening 194 and is slidably disposed within bore 193. The proximal portion of mixing rod 192 seats within recess or bore 193 and engages a spring 196 or other suitable biasing member disposed within the bore 193. A portion 197 of mixing rod 192 extends into chamber 181 for stirring the contents thereof. The spring 196 urges mixing portion 197 against the distal or end wall 177 of housing 172 and serves to retain the mixing portion 197 against such end wall 177 during advancement and retraction of plunger 182 relative to housing 172. An O-ring 197 or other suitable seal (not shown) can be provided in bore 193 proximal of piston seal 187 for inhibiting injectable material within chamber 181 from entering the bore 193. Alternatively, piston seal 187 can serve to seal bore 193 from injectable material within chamber 181. Mixing rod 192 can have any suitable cross-sectional shape. For example, the mixing rod 192 can have a circular cross-section, as shown in FIG. 14, or a rectangular cross-section so as to resemble a paddle, as shown in FIG. 15.

In operation and use of syringe 171 with medical device 21, fitting 173 can be coupled to fitting 88 of fluid connector 86 so that the material within syringe 171 can be supplied to needle 64 of injection device 26. Rotation by the user of twist knob 186 serves to advance plunger 182 into chamber 181 so as to expel the injectable material within the chamber from the syringe and, by means of needle member 61, into the tissue being treated. Precise delivery of injectable material from the syringe 171 into injection device 26 can be accomplished with the treaded syringe because each rotation of the twist knob 182 delivers a predetermined amount of the injectable material from passage 178 and thus needle opening 71. In addition, threaded syringe 171 permits relatively high and continuous material expulsion forces to be exerted by plunger 182 on the injectable material within chamber 181. For example, the syringe 171 can be used to generate pressures on the order of 100s of pounds per square inch. Such relatively high forces permit relatively viscous solutions or materials to be utilized as the injectable material of the present invention. Screw type syringe 171 further facilitates slow injections of material into the targeted tissue.

When a relatively viscous injectable material is utilized in the present invention, and thus relatively high pressures are required to push such material through needle member 61 and needle 64 thereof, sleeve 62 and the central portion 61c of needle member 61 can be reinforced so that the increase in pressure does not result in leaks in injection device 26. Such reinforcing also minimizes any stretching of sleeve 62 or the tubular material of central portion 61c and thus ensures that the translation of injectable material into proximal extremity 61a of the needle member 61 results in the translation of the same amount of material from opening 71 in needle 64. The reinforcing of the tubular members of needle member 61 and sleeve 62 further inhibits push back of needle member 61 relative to sleeve 62 when needle 64 is advanced into the targeted tissue. Such reinforcing further increases the column strength of sleeve 62 and the central portion 62c of needle member 61 so as to facilitate the clearing of any plugs that may develop in sleeve 62, particularly near sleeve distal extremity 62b. The reinforcing of sleeves 62 and the central portion 61c of needle member 61 can include increasing the hardness of the material of such tubular members.

As plunger 182 is advanced and retracted within chamber 181 of housing 172, stirring portion 197 of rod 192 serves to mix the injectable material within syringe 171. Mixing rod 192 is advantageously off center the plunger 182 so as not to be aligned with the exit passage 178 in end wall 177 and instead circumscribes the opening of such passage 178 and circulates within chamber 181 during rotation of plunger 182 relative to housing 172. Such mixing ensures a substantially constant consistency in the injectable material, which is particularly desirable when the injectable material includes a suspension. The utilization of a mixer in medical device 21 is particularly advantageous when the injectable material is slowly introduced into the targeted tissue, for example, by means of a syringe.

Other embodiments of the threaded syringe of the present invention can be provided. Threaded syringe 206 shown in FIGS. 16-18 is substantially similar to syringe 171 and like reference numerals have been used to described like components of syringes 206 and 171. The syringe 206 has a mixing member or mixer 207 with a stirring portion 208 which is U-shaped in configuration (see FIGS. 16 and 17). Mixer 207 is further provided with first and second end portions or legs 211 and 212 which seat within respective first and second recesses or bores 213 and 214 extending longitudinally into cylindrical body 183 of plunger 182. Piston seal 187 of the plunger 182 is provided with first and second openings 216 and 217 to respective first and second bores 213 and 214. First and second springs 196 are disposed within bores 213 and 214 and serve to urge stirring portion 208 against end wall 177 of the syringe housing 172. Stirring portion 208 is substantially centered on plunger 182 and in chamber 181 of the syringe body or housing 172. In an alternate embodiment of mixer 207, shown in FIG. 18, the distal end of stirring portion 208 is formed of an oblong or otherwise circular-type member 218 which is joined to first and second legs 211 and 212. Oblong member 218 preferably extends perpendicular to the first and second legs 211 and 212.

In operation and use, threaded syringe 206 can be utilized in substantially the same manner as described above with respect to threaded syringe 171. A first and second elongate portions or legs 211 and 212 of mixer 207 serve to increase the mixing action of the mixing member or mixer 207 relative to the single stirring portion 197 of mixing rod 192 of the threaded syringe 197. The relatively large engagement surface of stirring portion 208 against end wall 177 of the housing 172, and the even larger engagement surface of oblong member 218 against the end wall 177, serve to distribute the forces exerted by springs 196 over relatively large portions of the distal wall 177 and thus decrease the fictional forces between the mixer 207 and the syringe body or housing 172 during rotation of plunger 182.

Although threaded syringes 171 and 206 have been described for use with injection device 26, and can similarly be used with injection devices 126 and 151, if should be appreciated that fitting 173 of the syringe housing 172 can be coupled to any other injection means, needle assembly or needle and be within the scope of the present invention. For example, a conventional metal needle can be coupled to fitting 173. An exemplary procedure utilizing a threaded syringe 171 or 206 having a needle coupled to fitting 173 is the treatment of fecal incontinences, as more fully described in U.S. Pat. Nos. 6,251,063 and 6,595,901.

The medical device of the present invention can include a pressure indicator for monitoring the pressure of the fluid or other injectable material being translated therethrough for injection. Such a pressure indicator can be included as part of supply 27 or located at any other point of the flow path from supply 27 to the injection needle. In one preferred embodiment, a pressure indicator 226 is located between the supply of injectable material and the needle assembly or needle. Pressure indicator 226 is shown in FIG. 19 for use with a supply 27 which includes a screw type syringe 227 substantially similar to threaded syringes 171 and 206 described above. Like reference numerals have been used to describe like components of syringes 226, 171 and 206. Although syringe 227 can include a mixing member of any type, for example a mixing rod 192 or a mixer 207, the syringe 227 is shown without a mixer. In place of fitting 173 of syringes 171 and 206, syringe 227 includes a conventional female type fitting or connector 228 located at the distal end or base of housing 172. Passage 178 extends through connector 228.

Pressure indicator 226 is formed from a body 231 having a fluid passageway 232 extending longitudinally therethrough. The proximal end of body 231 includes a suitable connector or fitting in the form of a conventional male connector 233 for cooperatively coupling with connector 228 of the treaded syringe 227. The distal end of the body 231 is formed with any suitable fitting or connector such as a female connector 224 substantially similar to the female connector 228 of the syringe 227 for coupling the indicator 226 to any suitable needle or needle assembly. Fluid passageway 232 extends internally of body 231 between connectors 233 and 234. Pressure indicator or gage 226 includes a piston 236 slidably disposed within a chamber 237 formed in body 231. The chamber 237 communicates with fluid passageway 232 by means of an opening 238. Piston 236 is provided with a head 241 which can seat in chamber 237 at opening 238. The piston 236 further includes a rod 242 which extends from head 241 through chamber 237 and an opening 243 provided in body 231. A spring or other suitable biasing means 244 is disposed in chamber 237 around rod 242 and between head 241 and body 231 for urging the head against opening 243. A suitable seal (not shown) is provided between piston head 241 and body 231 for inhibiting the flow of material past the head 241 into chamber 237.

In operation and use, spring-loaded pressure indicator 226 is connected to threaded syringe 227 by means of male connector 233 and to a needle or needle assemblies such as injection device 26 by means of female connector 234 for coupling the threaded syringe 227 to medical device 21. As twist knob 186 is rotated by the operator to cause the injectable material to flow from chamber 237 of the syringe 227 into pressure indicator 226 and thereafter into injection device 26, pressure increases within internal or fluid passageway 232 of the indicator 226. Such increase of pressure causes piston head 241 to unseat and piston rod 242 to protrude further from opening 238. The amount that the piston rod 242 protrudes beyond opening 238, and thus the outside of body 231, correlates in a predetermined manner to the pressure of injectable fluid or other material within the indicator 226, and thus the pressure within the syringe 227 and injection device 26. Pressure readings from indicator 226 can serve to indicate a build up of pressure in injection device 26, for example as a result of a clog within passage 63 of needle member 61 or an impediment in the tissue of the wall 107 to the release of the injectable material from needle 64.

Other embodiments of the pressure indicator of the present invention can be provided. Pressure indicator 251 shown in FIG. 20 is also for use with threaded syringe 227. The pressure indicator 251 is substantially similar to pressure indicator 226 and like reference numerals have been used to describe like components of indicators 251 and 226. The indicator 251 is formed from a body 252 substantially similar to body 231 and having a chamber 253 therein which is substantially similar to the chamber 237 of body 231. In place of opening 238, body 252 is formed with an opening or hole 254 which communicates with chamber 253. A flexible, fluid-tight membrane 256 made from any suitable material such as rubber extends across the opening 254.

In operation and use, pressure indicator 251 is coupled to threaded syringe 227 and injection device 26 in the manner described above with respect to indicator 226. As twist knob 186 is rotated and the injectable material flows from syringe chamber 181 through fluid passageway 232 of body 252, injectable material flows through opening 238 into chamber 253. As pressure increases within internal passageway 232, flexible membrane 256 expands. The amount of such expansion of the flexible membrane 256 correlates in a predetermined manner to the pressure of the injectable material within the indicator 251 and thus the pressure within the syringe 227 and injectable device 26. As can be appreciated, the pressure indicators of the present invention can utilize any suitable mechanism with a variable that corresponds to the pressurized fluid used therewith.

Although pressure indicators 226 and 251 have been described for use with the injectable material of the present invention, it should be appreciated that such indicators can be utilized to measure the pressure of any suitable fluid dispensed by threaded syringe 227 or the other supply or reservoir utilized with the indicator 226 or 251. For example, pressure indicators 226 and 251 can be utilized with a supply of solvent, conditioning liquid or other fluid for injection into the tissue of a mammalian body or a solvent or other cleansing fluid for cleaning out the needle assembly or needle coupled to the pressure indicator.

A further pressure indicator of the present invention can be in the form of a clutch 261 included on the plunger 232 of the screw type syringe 227 (see FIG. 20). Clutch 261 can be located, for example, between the knurled twist knob 186 and the cylindrical body 183 of plunger 182. The clutch releases when the torque on twist knob 186 exceeds a predetermined amount corresponding to a predetermined pressure of the injectable fluid or other material within syringe 227. Upon release of the clutch 261, further twisting of knob 186 does not rotate or advance cylindrical body 183 of plunger 182.

As can be seen from the foregoing, a medical device for the delivery of an injectable material into the tissue of a mammalian body which permits increased accuracy in the placement of such material and the implants formed thereby has been provided. An injection device can be provided. The injection device can have a needle wherein retraction of the needle is limited during puncture of the tissue being treated. A port can be included in the injection device for facilitating cleaning thereof. The injection device can include first and second tubular members, wherein the first tubular member can be removed proximally from the second tubular member for cleaning the first tubular member in situ. The injection device can include a pressure indicator for monitoring the pressure of the injectable material. A syringe with a mixer can be provided. An injection needle can be provided. The needle can include at least one optic element for interrogating tissue in the vicinity of the treatment site. The needle can have a tapered distal surface with a large inclination angle for limiting the length of the distal opening in the needle.

What is claimed is:

1. An injection device for use with a probe having a longitudinally-extending passageway to treat muscle tissue of a mammalian body comprising a tubular member adapted for use with the probe and having an external diameter for permitting insertion into the passageway of the probe and an internal diameter, a needle assembly slidably disposed in the tubular member and having a central portion provided with an external diameter, the tubular member and needle assembly having respective proximal and distal extremities, the distal extremity of the needle assembly being provided with a needle and being extendable from the distal extremity of the tubular member and means carried by the proximal extremities of the tubular member and needle assembly for locking the proximal extremity of the needle assembly relative to the proximal extremity of the tubular member, the external diameter of the central portion of the needle assembly approximating the internal diameter of the tubular member and the needle assembly having a column strength when locked within the tubular member so that the needle assembly does not buckle within the tubular member during puncture of the muscle tissue by the needle and thereby limit retraction of the needle assembly relative to the tubular member during puncture of the muscle tissue and provide substantially one-to-one movement between the proximal and distal extremities of the needle assembly.

2. The device of claim 1 wherein the needle is made from metal, the needle assembly having an elongate portion made from plastic and terminating at a shoulder, the needle being attached to the elongate portion and extending forwardly of the shoulder.

3. The device of claim 1 wherein the needle assembly is provided with a passageway, at least one optical element disposed in the passageway.

4. The device of claim 3 wherein the at least one optical element includes a first optical element for supplying light to the tissue and a second optical element for receiving light reflected back by the tissue.

5. The device of claim 3 wherein the needle has a distal face lying in a plane and the at least one optical element has an end surface inclined at the angle and lying in the plane of the distal face.

6. The device of claim 1 wherein the needle assembly extends along a longitudinal axis and the needle has a distal face inclined at an angle greater than 25 degrees relative to the longitudinal axis.

7. The device of claim 6 wherein the distal face is inclined at an angle of approximately 30 degrees relative to the longitudinal axis.

8. The device of claim 1 wherein the needle assembly extends along a longitudinal axis and the needle has a distal face inclined at an angle to the longitudinal axis, the needle being provided with a bevel which intersects the distal face to form a sharpened tip.

9. The device of claim 1 further comprising a supply of at least one solution of a biocompatible composition and a biocompatible solvent coupled to the proximal extremity of the needle assembly for forming an implant in the tissue of the mammalian body.

10. The device of claim 9 wherein the biocompatible composition includes a bio compatible prepolymer.

11. The device of claim 9 wherein the at least one solution of the biocompatible composition and the biocompatible solvent has a composition comprising from about 2.5 to about 8.0 weight percent of a biocompatible polymer, from about 10 to about 40 weight percent of a water insoluble biocompatible contrast agent and from about 52 to about 87.5 weight percent of a biocompatible solvent.

12. An injection device for introducing a material into tissue of a mammalian body and for use with a probe having a longitudinally-extending passageway comprising a first tubular member adapted for use with the probe and having a diameter for permitting insertion of the first tubular member into the passageway of the probe, the first tubular member having a proximal extremity with a proximal opening and a distal extremity and being provided with a longitudinally-extending lumen extending from the proximal opening to the distal extremity, a second tubular member extending through the proximal opening of the first tubular member and being slidably disposed in the lumen of the first tubular member, the second tubular member having a proximal extremity and a distal extremity with a needle that is extendable from the distal extremity of the first tubular member, a reservoir of a solution of a biocompatible composition and a biocompatible solvent coupled to the proximal extremity of the second tubular member, the proximal extremity of the first tubular member having a port distal of the proximal opening, a reservoir of the biocompatible solvent coupled to the port for clearing any of the biocompatible composition that clogs the first tubular member distal of the port.

13. The device of claim 12 further comprising a fluid seal disposed between the first and second tubular members proximal of the port.

14. The device of claim 12 wherein the biocompatible composition includes a biocompatible prepolymer.

15. The device of claim 12 wherein the biocompatible composition includes a bio compatible polymer.

* * * * *